(12) United States Patent
Bornemann et al.

(10) Patent No.: US 11,648,149 B2
(45) Date of Patent: May 16, 2023

(54) SYSTEM AND METHOD FOR MAKING AN IMPLANT FOR AN EYE

(71) Applicant: ALCON INC., Fribourg (CH)

(72) Inventors: Stefan Bornemann, Nuremberg (DE); Thomas Deisinger, Cadolzburg (DE); Stefan Schmid, Neuendettelsau (DE)

(73) Assignee: Alcon Inc., Fribourg (CH)

( * ) Notice: Subject to any disclaimer, the term of this patent is extended or adjusted under 35 U.S.C. 154(b) by 870 days.

(21) Appl. No.: 16/529,609

(22) Filed: Aug. 1, 2019

(65) Prior Publication Data
US 2020/0069466 A1 Mar. 5, 2020

Related U.S. Application Data

(60) Provisional application No. 62/724,460, filed on Aug. 29, 2018.

(51) Int. Cl.
*A61F 2/16* (2006.01)
*A61F 9/00* (2006.01)
*A61F 9/008* (2006.01)
*B29D 11/02* (2006.01)
*B29D 11/00* (2006.01)
*A61K 9/00* (2006.01)

(52) U.S. Cl.
CPC ............ *A61F 9/0017* (2013.01); *A61F 2/16* (2013.01); *A61F 9/00804* (2013.01); *B29D 11/00942* (2013.01); *B29D 11/023* (2013.01); *A61F 2240/002* (2013.01); *A61K 9/0051* (2013.01)

(58) Field of Classification Search
None
See application file for complete search history.

(56) References Cited

U.S. PATENT DOCUMENTS

| | | |
|---|---|---|
| 2016/0038277 A1 | 2/2016 | Dai |
| 2017/0027754 A1 | 2/2017 | Muller |
| 2017/0212277 A1* | 7/2017 | Chapoy .................. G02B 1/041 |
| 2018/0290377 A1* | 10/2018 | Talken ................. C09D 11/322 |
| 2019/0240070 A1 | 8/2019 | Schmid et al. |
| 2019/0314145 A1 | 10/2019 | Schmid |

FOREIGN PATENT DOCUMENTS

WO 2016176444 A1 11/2016

* cited by examiner

*Primary Examiner* — Jacob T Minskey
*Assistant Examiner* — Adrien J Bernard

(57) ABSTRACT

In certain embodiments, a system for making an implant for an eye comprises a laser, a camera, and a computer. The laser emits a laser beam to shape a material. The camera generates one or more images to monitor shaping of the material. The computer stores a pattern for the implant, which is designed to provide refractive treatment for the eye; sends instructions to the laser to control the laser beam to shape the material according to the pattern; assesses the images from the camera according to the pattern; and adjusts the instructions in response to the images.

10 Claims, 3 Drawing Sheets

SYSTEM AND METHOD FOR MAKING AN IMPLANT FOR AN EYE

TECHNICAL FIELD

The present disclosure relates generally to refractive treatment of an eye, and more specifically to systems and methods for making an implant for an eye.

BACKGROUND

Refractive treatment of an eye refers to techniques performed to change the refractive properties of the eye to reduce refractive error to improve vision. Refractive error occurs when parts of the eye do not bend light correctly, resulting in a blurred image. The main types of refractive errors are myopia (nearsightedness), hyperopia (farsightedness), presbyopia (loss of near vision with age), and astigmatism. Ocular implants are used in one type of refractive treatment. An ocular implant is implanted into the eye to change the refractive properties to improve vision.

BRIEF SUMMARY

In certain embodiments, a system for making an implant for an eye comprises a laser, a camera, and a computer. The laser emits a laser beam to shape a material. The camera generates one or more images to monitor shaping of the material. The computer stores a pattern for the implant, which is designed to provide refractive treatment for the eye; sends instructions to the laser to control the laser beam to shape the material according to the pattern; assesses the images from the camera according to the pattern; and adjusts the instructions in response to the images.

In certain embodiments, a method for making an implant for an eye includes accessing a pattern for the implant designed to provide refractive treatment for the eye. Instructions are sent to a laser to control a laser beam to shape a material according to the pattern. One or more images of the material are generated to monitor the shaping of the material. The images are assessed according to the pattern, and the instructions are adjusted in response to the images.

Embodiments of systems and methods may include none, one, some, or all of any of the following features:

The laser ablates the material and/or creates incisions in the material to shape the material.
The camera comprises an optical coherence tomography (OCT) system, a Scheimpflug system, or a stereoscopic camera system.
A printer can print the material, where the printer has a printer head that deposits the material onto a stage.
A curing illuminator can direct a curing light towards the material.
The computer can assess the images from the camera according to the pattern by: identifying a shape of the material in the image; and comparing the identified shape with a shape defined by the pattern.
The computer can adjust the instructions in response to the image by instructing the laser to remove unwanted material.
The material comprises a biological or biocompatible material.

BRIEF DESCRIPTION OF THE DRAWINGS

Embodiments of the present disclosure are described by way of example in greater detail with reference to the attached figures, in which.

DESCRIPTION OF EXAMPLE EMBODIMENTS

Referring now to the description and drawings, example embodiments of the disclosed apparatuses, systems, and methods are shown in detail. As apparent to a person of ordinary skill in the field, the disclosed embodiments are exemplary and not exhaustive of all possible embodiments.

Figure 1:
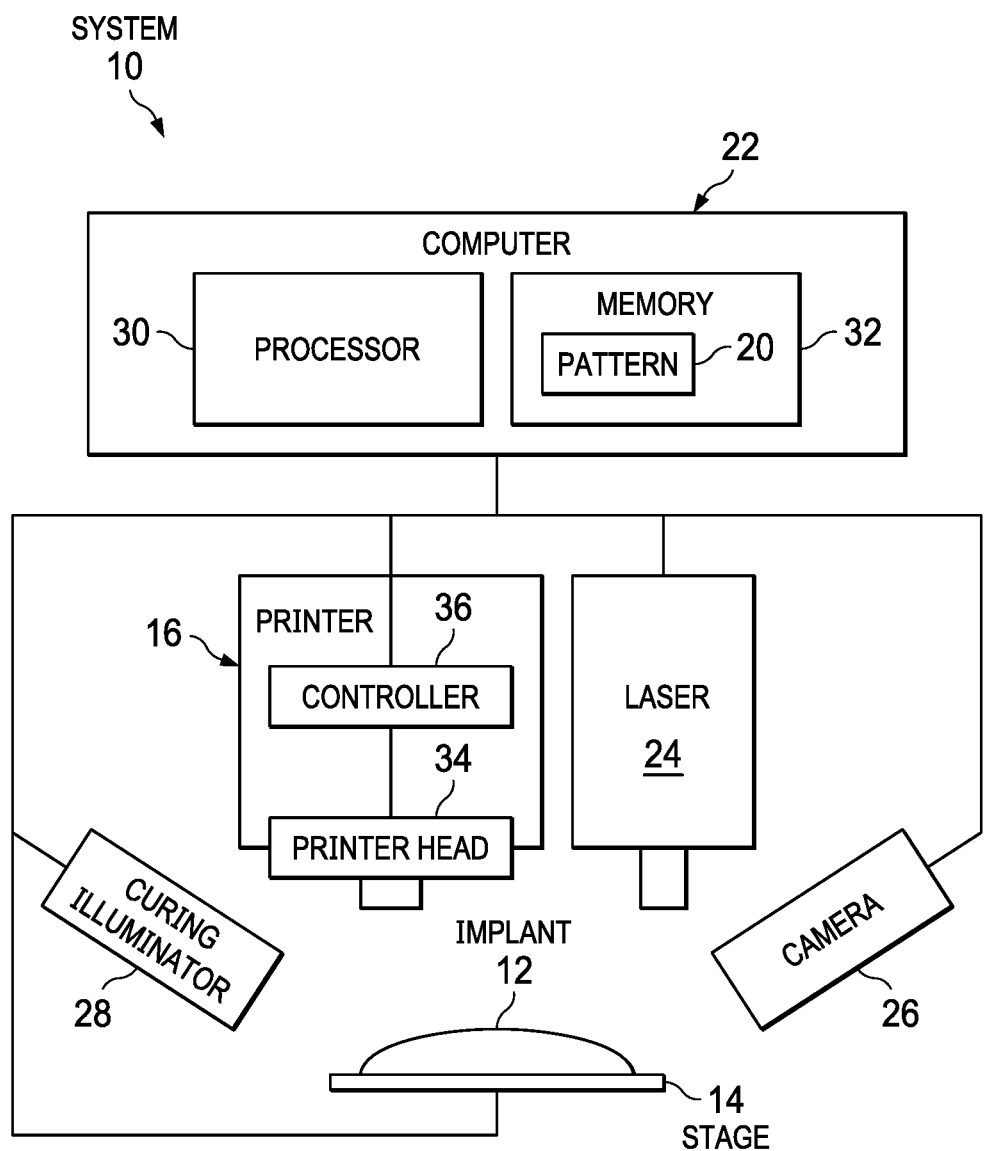
FIG. 1 illustrates an example of a system for making an implant for an eye.

FIG. 1 illustrates an example of a system 10 for making an implant 12 for an eye. System 10 includes a computer 22 that accesses a pattern 20 for an implant designed to provide refractive treatment for an eye. A laser 24 emits a laser beam to shape a biological or biocompatible material. Computer 22 sends instructions to laser 24 to control the laser beam to shape the material according to the pattern. A camera 26 generates images to monitor the shaping of the material. Computer 22 assesses the images from camera 26 according to pattern 20, and adjusts the instructions in response to the images.

To aid in description, this description refers a coordinate system used in laser eye surgery. In this coordinate system, the direction in which the laser beam is emitted defines the z-axis, and the xy-plane is the plane normal to the z-axis.

As an overview of the embodiment, system 10 comprises computer 22, a printer 16, a stage 14, laser 24, camera 26, and a curing illuminator 28 coupled as shown. Computer 22 includes one or more processors 30 and one or more memories 32 that store pattern 20. Printer 16 includes a printer head 34 and a printer controller 36. In operation, computer 22 sends instructions to the components of system 10 to tell the components how to make implant 12 according to pattern 20. Printer 16 prints material onto the target. Laser 24 shapes the material according to pattern 20. Curing illuminator 28 illuminates the material with a light that promotes curing of the material. Stage 14 is a platform that supports the material while system 10 makes the implant. Camera 26 generates images to monitor the creation of implant 12.

Implant 12 is an ocular implant, i.e., an artificial aid surgically implanted into an eye to provide refractive treatment for the eye. When implant 12 is implanted into an eye and the eye recovers from the implantation, implant 12 changes the refractive properties of the eye to improve vision. Examples of implant 12 include a corneal inlay, corneal onlay, intraocular lens, or corneal transplant. In the case of a corneal transplant, system 10 creates "donor" tissue that may include cell layers like epithelial, Bowman, stromal, and/or endothelial cells. Donor tissue may be created for a full thickness cornea transplant (i.e., a penetrating keratoplasty) or a back layer cornea transplant (i.e., an endothelial keratoplasty).

Implant 12 may have any suitable size or shape. For example, implant 12 may be circular or annular with a diameter in the range of 0.5 to 12 millimeters (mm), or in a sub-range such as 0.5 to 5 mm, 5 mm to 8 mm, or 8 to 12 mm. In certain embodiments, implant 12 may comprise material printed on a transparent biocompatible substrate. (Examples of such material are described below.) In other embodiments, implant 12 may comprise the material, but not a substrate. An effective area of an implant 12 may be the area through which the eye sees, e.g., the area circumscribed by the pupil at its largest size.

Pattern 20 describes the external size and shape of implant 20 and may also describe internal structures of implant 20. Internal structures may result from how material is deposited, cured, and/or shaped during creation of implant 20. In certain embodiments, pattern 20 may define how material should be deposited, cured, and/or shaped at each layer that forms implant 20. For example, pattern 20 may define how a first layer should be made by describing where material should be deposited, whether and how the material should be cured, and/or whether and how the material should be shaped. Pattern 20 may define how subsequent layers should be made using a similar type of description. Examples of implants 12, internal structures, and patterns 20 are illustrated in FIGS. 3A to 4C.

Printer 16 may be any suitable printer configured to deposit material onto a target according to digital instructions. For example, printer 16 may be a 3D (or additive manufacturing) printer that deposits successive layers of material to yield material configured in a specific shape and size. Printer 16 includes printer head 44 and printer controller 46. Printer head 44 directs material onto the target and may be any suitable printer extruder that deposits material onto a surface. Printer controller 46 moves the printer head in the x, y, z directions to direct the material onto a specific location of the target, and may receive instructions from computer 22 to move the printer head 44 according to pattern 20. Examples of printer 16 include bio-extrusion, inkjet/micro-valve, electrospinning, or laser-aided printers.

Printer 16 prints material that comprises any suitable transparent or semitransparent material that is biological and/or biocompatible. Examples of such material include cultivated collagen material, human or animal cell material, biocompatible plastic, hyaluronan, recombinant human collagen III (RHCIII), gelatin methacrylate, and silk. In certain cases, a material over which the epithelium can grow may be used. Such material may provide optimal nutrition of corneal cells and extra-cellular material, optical transparency over lifetime, and supportive surface properties for epithelium growth.

Printer 16 prints material onto a target, which may be stage 14 or an implant substrate supported by stage 14. In certain embodiments, an implant substrate may be a mold that shapes the surface of material that is deposited on the mold. The mold may be removed prior to implantation of implant 12 into an eye. In other embodiments, an implant substrate may form a part of implant 20, and is implanted into an eye with the rest of the implant 20. In these embodiments, the implant substrate may comprise a transparent or semitransparent material that is biological and/or biocompatible, as described above.

Laser 24 shapes the material according to pattern 20. Laser 24 may be any suitable laser device that generates and emits a laser beam that can shape the material. For example, laser 24 may be an excimer laser that ablates the material to shape it. As another example, laser 24 may be a femto laser that photodisrupts the material to create incisions in the material. The incisions may separate material to be removed from the implant. Laser 24 may comprise a laser source (e.g., excimer or femto) that generates a laser beam, and scanning components (e.g., optics) that direct the focus of the laser beam to specific points of the target. Computer 22 may instruct laser 24 to shape the material by describing where the material should be removed, e.g., by ablation or by incisions.

Curing illuminator 28 comprises a light source that directs a curing light towards the material to cure the material. The light may cure the material by promoting cross-linking of the material. Examples of curing light include ultraviolet light or light (such as LED light) between 400 to 500 nm. Computer 22 may instruct curing illuminator 28 to cure material by indicating when the material should be cured, the curing time, and/or the curing intensity.

Camera 26 generates images of the material to monitor the printing of the material. Camera 26 may comprise any suitable system that can generate an image of an object. An optical coherence tomography (OCT) system (such as a time domain or frequency domain OCT system) that generates OCT scans to generate the image is an example of camera 26. Other examples include a Scheimpflug system (light section measurement) or a stereoscopic camera system.

Computer 22 sends instructions to the components of system 10 to tell the components how to make implant 12 according to pattern 20. For example, computer 22 sends instructions to laser 24 to shape the material according to pattern 20. In certain embodiments, computer 22 sends instructions to printer controller 36 to move printer head 34 to print the material according to pattern 20, and/or to curing illuminator 28 to direct the curing light according to pattern 20.

In addition, computer 22 assesses images from camera 26 and can adjust the instructions in response to the image. Computer 22 may assess the image according to pattern 20 by comparing the image to pattern 20 to determine differences between the image and pattern 20. Computer 22 may image process the image to identify features of the image that correspond to the same features of implant 12 defined by pattern 20. The features may be, e.g., an external shape or size or an internal structure. The corresponding features are compared to detect any differences. If a difference is detected, the instructions may be adjusted to reduce the difference. For example, if the image shows material where pattern 20 indicates there should be no material, computer 22 may send instructions to laser 24 to remove the unwanted material. As another example, if the image shows no material where pattern 20 indicates there should be material, computer 22 may send instructions to printer 16 to deposit more material.

Computer 22 may perform the assessment and adjustment at any suitable time during the creation of implant 12. For example, computer 22 may continually perform the assessment and adjustment, or may perform the assessment and adjustment at certain times, e.g., periodically.

Figure 2:
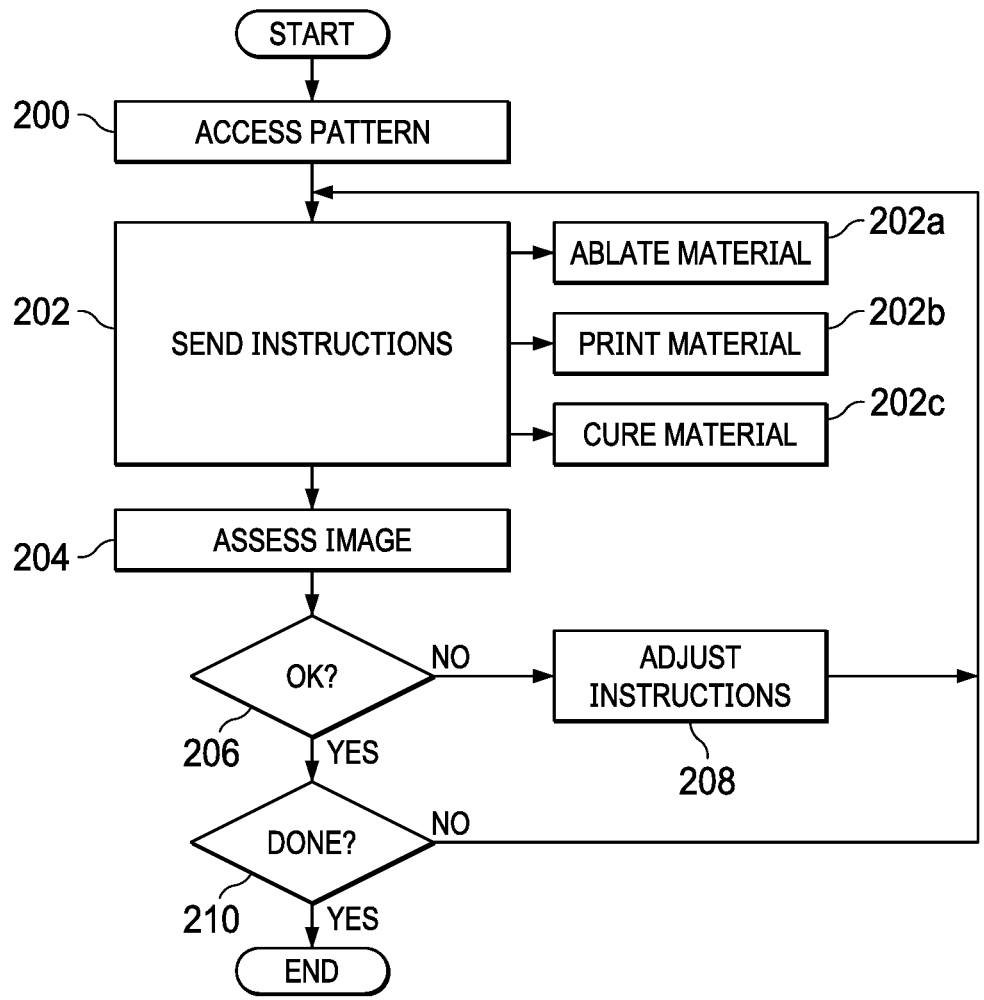
FIG. 2 illustrates another example of a method for making an implant 12 for an eye, which may be performed by system 10 of FIG. 1.

FIG. 2 illustrates another example of a method for making an implant 12 for an eye, which may be performed by system 10 of FIG. 1. The method starts at step 200, where computer 22 accesses pattern 20 for making ocular implant 12 from a given block of material supported by stage. Computer 22 sends instructions to components of system 10 at step 202 to make implant 12 according to pattern 20. For example, computer 22 sends instructions to laser 24 at step 202*a* to ablate the material or create incisions in the material to shape the material according to pattern 20. In certain embodiments, computer 22 may send instructions to printer 16 at step 202*b* to print more material onto the block of material to continue shaping the material and/or to curing illuminator 28 at step 202*c* to direct the curing light towards the material. In certain embodiments, computer 22 may send instructions to a user (e.g., via a display or verbal command) or to a robotic arm to turn the material to allow laser 24 to shape another side of the material.

Camera 26 generates images of the material, and computer 22 assesses the images at step 204. Computer 22 may assess the image according to pattern 20 by comparing the image to pattern 20 to determine differences between a feature (e.g., an external shape or size) of the image and a corresponding feature defined by pattern 20. For example, computer 22 may identify a shape of the material in the image, and compare the identified shape with a shape defined by the pattern.

Computer 22 determines if the material is satisfactory at step 206. The material may be satisfactory if there are no differences or only negligible differences between the features. A negligible difference may be a difference that causes no noticeable difference in the resulting vision.

If the material is not satisfactory at step 206, the method proceeds to step 208, where computer 22 adjusts the instructions in response to the image. The instructions may be adjusted to reduce the difference between the imaged feature and the pattern feature. For example, instructions may be adjusted to remove unwanted material by ablation or by creating incisions.

If the material is satisfactory at step 206, the method proceeds to step 210, where computer 22 determines if the implant forming process is finished. If the process is not finished, the method returns to step 202 to send more instructions. If the process is finished, the method ends.

Figure 3A:
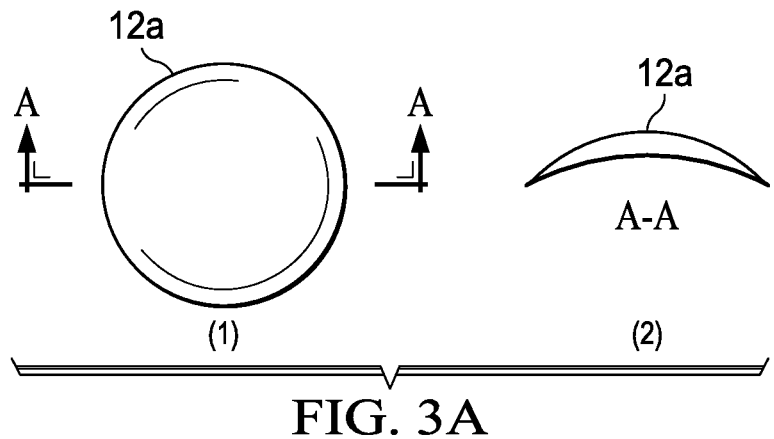
FIGS. 3A and 3B illustrate examples of implants 12 with different external shapes that may be made by system 10 of FIG. 1.
Figure 3B:
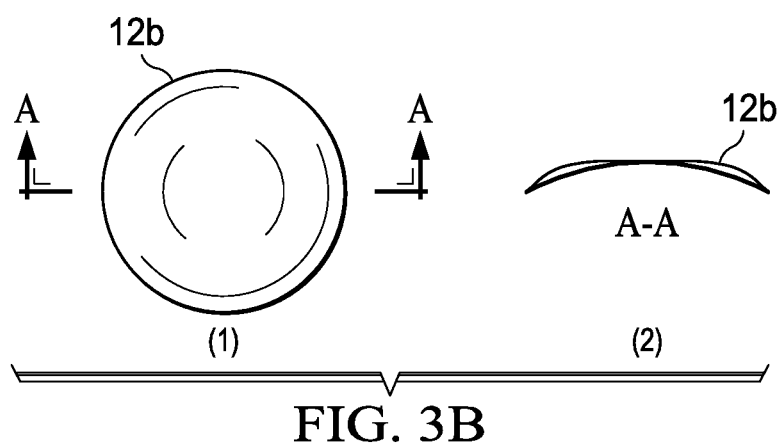

FIGS. 3A and 3B illustrate examples of implants 12 with different external shapes that may be made by system 10 of FIG. 1. Implant 12a of FIG. 3A may be used for correction of hyperopia, and implant 12b of FIG. 3B may be used for correction of myopia. FIGS. 3A(1) and 3B(1) illustrate a top view of implants 12a and 12b, respectively, and FIGS. 3A(2) and 3B(2) illustrate a cross-section view of implants 12a and 12b, respectively, along line A-A.

A component (e.g., a computer) of the systems and apparatuses disclosed herein may include an interface, logic, and/or memory, any of which may include hardware and/or software. An interface can receive input to the component, provide output from the component, and/or process the input and/or output. Logic can perform the operations of the component, e.g., execute instructions to generate output from input. Logic may be a processor, such as one or more computers or one or more microprocessors. Logic may be computer-executable instructions encoded in memory that can be executed by a computer, such as a computer program or software. A memory can store information and may comprise one or more tangible, non-transitory, computer-readable, computer-executable storage media. Examples of memory include computer memory (e.g., Random Access Memory (RAM) or Read Only Memory (ROM)), mass storage media (e.g., a hard disk), removable storage media (e.g., a Compact Disk (CD) or a Digital Video Disk (DVD)), and network storage (e.g., a server or database).

Although this disclosure has been described in terms of certain embodiments, modifications (such as substitutions, additions, alterations, or omissions) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, and the operations of the systems and apparatuses may be performed by more, fewer, or other components. As another example, modifications may be made to the methods disclosed herein. The methods may include more, fewer, or other steps, and the steps may be performed in any suitable order.

What is claimed is:

1. A system for making an implant for an eye, comprising:
   a printer configured to print a material for making the implant, the material distinct from eye tissue, the printer comprising a printer head configured to deposit the material;
   a laser configured to emit a laser beam to shape the material;
   a camera configured to generate one or more images to monitor the shaping of the material;
   a computer configured to:
      store a pattern for the implant, the implant designed to provide refractive treatment for the eye;
      send instructions to the printer to deposit the material according to the pattern for the implant designed to provide the refractive treatment for the eye;
      send instructions to the laser to control the laser beam to shape the material according to the pattern for the implant designed to provide the refractive treatment for the eye;
      assess the images of the shaping of the material from the camera according to the pattern; and
      adjust the instructions to the printer and the laser in response to the assessment of the images of the shaping of the material to yield the implant designed to provide the refractive treatment for the eye.

2. The system of claim 1, the laser configured to ablate the material to shape the material.

3. The system of claim 1, the laser configured to create incisions in the material to shape the material.

4. The system of claim 1, the camera comprising an optical coherence tomography (OCT) system.

5. The system of claim 1, further comprising a curing illuminator configured to direct a curing light towards the material.

6. The system of claim 1, wherein the computer is configured to assess the images from the camera according to the pattern by:
   identifying a shape of the material in the image; and
   comparing the identified shape with a shape defined by the pattern.

7. The system of claim 2, wherein the computer is configured to adjust the instructions in response to the image by:
   instructing the laser to remove unwanted material.

8. The system of claim 1, the material comprising a biological or biocompatible material.

9. The system of claim 1, wherein the implant is designed to treat hyperopia.

10. The system of claim 1, wherein the implant is designed to treat myopia.

* * * * *